United States Patent
Scholz

[11] Patent Number: 5,654,339
[45] Date of Patent: Aug. 5, 1997

[54] USE OF PROSTANE DERIVATIVES OF FORMULATE I AND II FOR TREATMENT OF CHRONIC POLYARTHRITIS

[75] Inventor: Peter Scholz, Berlin, Germany

[73] Assignee: Schering Aktiengesellschaft, Berlin, Germany

[21] Appl. No.: 416,843

[22] PCT Filed: Aug. 9, 1993

[86] PCT No.: PCT/DE93/00722

§ 371 Date: Jun. 9, 1995

§ 102(e) Date: Jun. 9, 1995

[87] PCT Pub. No.: WO94/03175

PCT Pub. Date: Feb. 17, 1994

[30] Foreign Application Priority Data

Aug. 7, 1992 [DE] Germany ............ 42 26 615.7
Aug. 19, 1992 [DE] Germany ............ 42 27 788.4

[51] Int. Cl.[6] ............ A61K 31/19; A61K 31/557
[52] U.S. Cl. ............ 514/573
[58] Field of Search ............ 514/573

[56] References Cited

U.S. PATENT DOCUMENTS 5,506,265 4/1996 Blitstein-Willinger ............ 514/573

*Primary Examiner*—Theodore J. Criares
*Attorney, Agent, or Firm*—Millen, White, Zelano & Branigan, P.C.

[57] ABSTRACT

The invention relates to the use of prostane derivatives general formula I

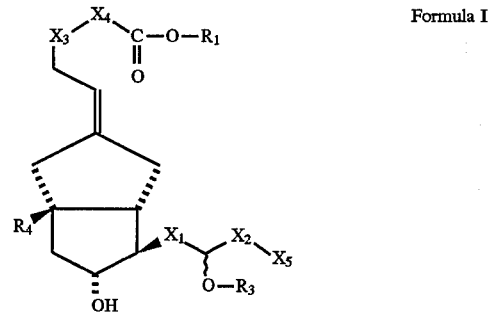

in which
$X_1$ is a —$CH_2$—$CH_2$— or trans —CH=CH—,
$X_2$ is a straight-chain or branched, saturated alkylene group with 1 to 6 carbon atoms,
$X_3$ is a —$CH_2$—,
$X_4$ is a —$CH_2$—,
$X_5$ is a —C≡C—$R_2$;
$R_1$ is a hydrogen atom, an alkyl group with 1 to 6 carbon atoms, a cycloalkyl group with 5 or 6 carbon atoms, or a phenyl group,
$R_2$ is a straight-chain or branched-chain, saturated or unsaturated alkyl group with 1 to 6 carbon atoms,
$R_3$ is a hydrogen atom or an acyl radical with 1 to 4 carbon atoms, and
$R_4$ is an —H;
in which the —O—$R_3$ group is in α- or β-position, and their salts with physiologically compatible bases, if $R_1$ indicates a hydrogen atom, for the production of a pharmaceutical agent for the treatment of chronic polyarthritis.

17 Claims, No Drawings

USE OF PROSTANE DERIVATIVES OF FORMULATE I AND II FOR TREATMENT OF CHRONIC POLYARTHRITIS

This application is filed under 35 U.S.C. 371 and claims priority of PCT/DE93/00722 filed Aug. 9, 1993, and claims priority to Federal Republic of Germany application P 42 27 788.4 filed Aug. 19, 1992.

The invention relates to the use of prostane derivatives for the production of a medicament for the treatment of an immunologic response.

BACKGROUND OF THE INVENTION

Several prostane derivatives and their production are described in publication EP 0 011 591 (date of application: Oct. 18, 1979). These prostane derivatives are compounds that are derived from prostacyclin ($PGI_2$). They contain a methylene group instead of the 9-ether-oxygen atom in prostacyclin. Prostane derivatives are used for the treatment of various diseases; in this connection the cardiovascular and thrombo-aggregation-inhibiting effect is clearly emphasized.

The use of prostane derivatives as medicaments is described in detail in European publication EP 0 011 591: Lowering of peripheral, arterial, and coronary vascular resistance, inhibition of platelet aggregation and dissolution of platelet thrombi, myocardial cytoprotection and thus lowering of systemic blood pressure without reducing cardiac output and coronary blood circulation at the same time; treatment of stroke, prophylaxis and treatment of coronary heart disease, coronary thrombosis, myocardial infarction, peripheral arterial diseases, arteriosclerosis and thrombosis, treatment of shock, inhibition of bronchoconstriction, inhibition of stomach acid secretion and cytoprotection of the mucous membrane of the stomach and intestines; anti-allergic properties, lowering of pulmonary vascular resistance and of pulmonary blood pressure, stimulation of renal blood circulation, use to replace heparin or as an adjuvant in the dialysis of hemofiltration, preservation of dried blood plasma, especially of dried blood platelets, inhibition of labor pains, treatment of gestational toxicosis, antiproliferative effect, and improvement of cerebral blood circulation.

Carbacyclin derivatives are listed in publications EP-0 055 208, EP-0 099 538, and EP-0 119 949, which have indications similar to those of the above-mentioned prostane derivatives.

Publication EP 0 084 856 describes other prostane derivatives which were proposed for use in inhibiting platelet aggregation, lowering systemic blood pressure, or treating gastric ulcers. In particular, beraprost is mentioned in it.

The use of prostane derivatives for the treatment of immunologic responses is described in various publications. Thus, the treatment of anti-allergic properties is mentioned in passing even in European Publication EP 0 011 591.

European Publication EP 0 055 208 describes, i.a., the anti-allergic effect of carbacyclin derivatives.

In the publication by H. J. GRUNDMANN et al. (1992) J. Infect. Dis. 1992, 165: 1–5, the use of a prostane derivative, namely iloprost, in the treatment of septic shock is explained in detail.

In international patent application PCT/DE 92/00100 (date of application of the priority-justifying application: Feb. 12, 1991 in the Federal Republic of Germany), treating AIDS and diabetes with the help of prostane derivatives is mentioned. This application is prior law.

The K. SLIWA et al. (1991) publication Infection and Immunity, 59: 3846–3848 deals with the treatment of cerebral malaria with iloprost.

SUMMARY OF THE INVENTION

It has now been found, surprisingly enough, that prostane derivatives can be used in the case of another indication.

The invention relates to a use of prostane derivatives of general formula I or II

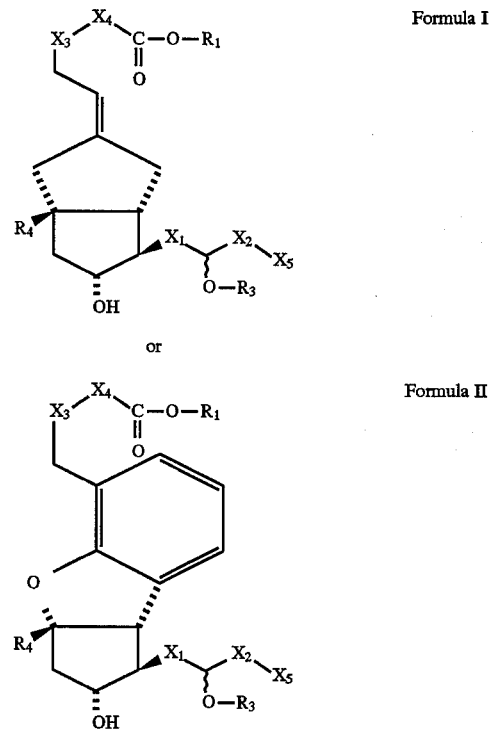

Formula I

Formula II in which $X_1$ is a $-CH_2-CH_2-$; trans $-CH=CH-$ or $-C\equiv C-$, $X_2$ is a straight-chain or branched, saturated alkylene group with 1 to 6 carbon atoms, $X_3$ is an $-O-$ or $-CH_2-$, $X_4$ is a $-CH_2-$ or $-[CH_2]_3-$, $X_5$ is an $-H$ or $-C\equiv C-R_2$;

$R_1$ is a hydrogen atom, an alkyl group with 1 to 6 carbon atoms, a cycloalkyl group with 5 or 6 carbon atoms, or a phenyl group, $R_2$ is a straight-chain or branched-chain, saturated or unsaturated alkyl group with 1 to 6 carbon atoms, $R_3$ is a hydrogen atom, an acyl radical with 1 to 4 carbon atoms, or a benzoyl radical, and $R_4$ is an $-H$ or $-CH_3$;

in which the $-O-R_3$ group is in $\alpha$- or $\beta$-position, and their salts with physiologically compatible bases, if $R_1$ has the meaning of a hydrogen atom, for the production of a pharmaceutical agent for the treatment of chronic polyarthritis.

$X_2$ stands for straight-chain or branched, saturated alkylene groups with 1 to 6 carbon atoms, for example, methylene, ethylene, propylene, isopropylene, and the methyl group is connected to the first or second carbon atoms of the ethylene, counting from group A: butylene, methylpropylene, ethylethylene, dimethylethylene, and the methyl or ethyl group is connected as desired to the alkylene chain; pentyl, methylbutylene, dimethylpropylene, ethylpropylene, methylethylethylene, in which the methyl or ethyl group is connected as desired to the alkylene chain; hexylene, methylpentylene, dimethylbutylene, methylethylpropylene, in which the methyl or ethyl group is connected as desired to the alkylene chain.

Alkyl group $R_1$ comprises straight or branched alkyl groups with 1 to 6 carbon atoms, such as, for example, methyl, ethyl, propyl, butyl, isobutyl, tert-butyl, pentyl, neopentyl, hexyl.

Cycloalkyl group $R_1$ can contain 5 or 6 carbon atoms in the ring.

Alkyl group $R_2$ can consist of straight-chain or branched-chain, saturated or unsaturated alkyl radicals with 1 to 6 carbon atoms; the alkyl radicals are preferably saturated. For example, methyl, ethyl, propyl, butyl, isobutyl, tert-butyl, pentyl, hexyl, butenyl, isobutenyl, propenyl, pentenyl or hexenyl groups can be mentioned.

Acyl group $R_3$ can consist of a straight-chain or branched-chain acyl group with 1 to 4 carbon atoms, such as, for example, acetyl, propionyl, butyryl, or isobutyryl.

The invention also relates to a process for the treatment of chronic polyarthritis in humans and mammals that require such a treatment, where the treatment involves administration of a pharmacologically safe and effective amount of the prostane derivatives according to formula I or II in humans and mammals.

Inorganic and organic bases, as they are known to one skilled in the art for the formation of physiologically compatible salts, are suitable for forming salts with free acids. For example, there can be mentioned: alkali hydroxides, such as sodium and potassium hydroxide, alkaline-earth hydroxides, such as calcium hydroxide, ammonia, amines, such as ethanolamine, diethanolamine, triethanolamine, N-methylglucamine, morpholine, tris-(hydroxymethyl)-methylamine, etc. B-cyclodextrin clathrate formation takes place according to EP 0 259 468.

Chronic polyarthritis is a joint disease in which the synovial tissue has a destructive effect on the matrix of the articular cartilage. In the synovial tissue and the synovial fluid of patients with chronic polyarthritis, there are activated cells which secrete cytokines such as TNF-α and Il-1. Both cytokines, TNF-α and Il-1, are able to induce the production of collagenase and other neutral proteases in synovial fibroblasts and chondrocytes that are located near the articular cartilage. These enzymes degrade proteoglycans and collagen, which leads to destruction of the cartilage. (TNF-α=tumor necrosis factor-α; Il-1=interleuin 1).

Surprisingly enough, prostane derivatives are suitable for the treatment of chronic polyarthritis. Previously, substances such as carboxylic acids (salicylates, arylacetic acids, fenamates, propionic acids), pyrazolones, and oxicams were used for treatment. (Handbook of Experimental Pharmacology, 1979, Springer Verlag, Vol. 50/II, Editors: G. V. R. BORN et al., Chapter 30, Anti-Inflammatory Drugs, J. R. VANE, S. H. FERREIRA, Chapter 32, Classification of Antirheumatic Drugs, E. C. HUSKISSON, Chapter 37, M. K. JASANI).

The use of prostane derivatives according to the invention is preferred with the above-mentioned general formula I in which $X_1$ is a trans —CH=CH—, $X_2$ is a straight-chain or branched, saturated alkylene group with 2 to 4 carbon atoms, $X_3$ is a —CH$_2$—, $X_4$ is a —CH$_2$—, $X_5$ is a —C≡C—R$_2$;

$R_1$ is a hydrogen atom, an alkyl group with 1 to 3 carbon atoms or phenyl group, $R_2$ is a straight-chain or branched-chain, saturated or unsaturated alkyl group with 1 to 3 carbon atoms, $R_3$ is a hydrogen atom or an acyl radical with 2 carbon atoms and $R_4$ is an —H;

in which the —O—R$_3$ group is in α- or β-position, and their salts with physiologically compatible bases, if $R_1$ indicates a hydrogen atom, for the production of a pharmaceutical agent for the treatment of chronic polyarthritis.

More preferred is the use of prostane derivatives according to the invention with the above-mentioned general formula I in which $X_1$ is a trans —CH=CH—, $X_2$ is a methylethylene group, in which the methyl group is connected to the first carbon atom of the ethylene group and the first carbon atom of the ethylene group is assigned to group A, $X_3$ is a —CH$_2$—, $X_4$ is a —CH$_2$—, $X_5$ is a —C≡C—R$_2$;

$R_1$ is a hydrogen atom or a methyl group, $R_2$ is a methyl or ethyl group, $R_3$ is a hydrogen atom or a formyl group and $R_4$ is an —H;

in which the —O—R$_3$ group is in α- or β-position, and their salts with physiologically compatible bases, if $R_1$ indicates a hydrogen atom, for the production of a pharmaceutical agent for the treatment of chronic polyarthritis.

Most preferred is the use of a prostane derivative according to the invention having the above-mentioned general formula I in which $X_1$ is a trans —CH=CH—, $X_2$ is a methylethylene group, in which the methyl group is connected to the first carbon atom of the ethylene group and the first carbon atom of the ethylene group is assigned to group A, $X_3$ is a —CH$_2$—, $X_4$ is a —CH$_2$—, $X_5$ is a —C≡C—R$_2$;

$R_1$ is a hydrogen atom, $R_2$ is a methyl group, $R_3$ is a hydrogen atom and $R_4$ is an —H;

in which the OH group is in α- or β-position, and its salts with physiologically compatible bases, for the production of a pharmaceutical agent for the treatment of chronic polyarthritis.

This substance has the name "iloprost" and bears the systematic designation 5-(E)-(1S,5S,6R)-7-hydroxy-6[(E)-(3S,4RS)-3-hydroxy-4-methyl-1-octen-6-inyl]bicyclo [3.3.0]octen-3-ylidene pentanoic acid. It is the most preferred compound of this invention.

The invention further comprises the use of the preferred substances cicaprost, eptaloprost, ciprostene and/or beraprost and their salts for the production of a pharmaceutical agent for the treatment of chronic polyarthritis. The substances, including iloprost, are listed to show their structures in Table 1.

The invention further relates to the use of prostane derivatives according to the invention together with pharmacological adjuvants and vehicles that are physiologically compatible. Such substances are described in Remington's Pharmaceutical Science, 15th ed., Mack Publishing Company, Easton, Pa. (1980).

The production processes for some of the prostane derivatives according to the invention are described in detail in publication EP 0 011 591 or EP 0 084 856. However, the substances of formula I or II that are not expressly mentioned there do not differ as regards the production process. They can be produced by one skilled in the art in the context of general knowledge.

(1984) Biochem. Pharmac. 33: 1263–1271, further K. KELLER et al. (1990), J. Orthop Res. 8: 345–352). The in vitro system is complex, so that it is representative of the clinical picture in chronic polyarthritis.

The compounds of general formula I or II are suitable for the treatment of chronic polyarthritis.

For this therapeutic effect, the suitable dose differs and depends, for example, on the compound of general formula I or II that is used, the host, the type of administration, and the type and severity of the conditions to be treated, but in general, satisfactory results are to be expected in animals with daily doses of 1 to 3000 µg/kg of animal body weight. With large mammals, e.g., humans, there is a recommended

TABLE 1

Structures of the Preferred Prostane Derivatives

| Designation | Formula I or II | $X_1$ | $X_2$ | $X_3$ | $X_4$ | $X_5$ | $R_1$ | $R_2$ | $R_3$ | $R_4$ |
|---|---|---|---|---|---|---|---|---|---|---|
| Iloprost | (I) | $-CH=CH-$ | $CH_3$ (branched) | $-CH_2=$ | $-CH_2-$ | $-C\equiv C-R_2$ | H | $-CH_3$ | H | H |
| Cicaprost | (I) | $-C\equiv C-$ | $CH_3$ (branched) | $-O-$ | $-CH_2-$ | $-C\equiv C-R_2$ | H | $-CH_2-CH_3$ | H | H |
| Eptaloprost | (I) | $-C\equiv C-$ | $CH_3$ (branched) | $-O-$ | $-(CH_2)_3-$ | $-C\equiv C-R_2$ | H | $-CH_2-CH_3$ | H | H |
| Ciprostene | (I) | $-CH=CH-$ | $n-C_5H_{10}$ | $-CH_2-$ | $-CH_2-$ | H | H | — | H | $-CH_3$ |
| Beraprost | (II) | $-CH=CH-$ | $CH_3$ (branched) | $-CH_2-$ | $-CH_2-$ | $-C\equiv C-R_2$ | H | $-CH_3$ | H | H |

The compounds of general formula I or II can be used effectively in the test below:

Cells from the synovial fluid of patients with chronic polyarthritis are co-cultivated in vitro with 4-day-old limb buds of mouse embryos (12 days). After co-cultivation for about 7 days, degradation of the cartilage in the limb buds occurs; this degradation can be reduced in the presence of the prostane derivatives according to the invention.

The degradation of the cartilage is measured by the release of sulfated glycosaminoglycans, which are quantified as alcian blue glycosaminoglycan complex.

The prostane derivatives according to the invention reduce the release of glycosaminoglycans, in which case the release is induced via the synovial cells.

Electron microscope examination of cartilage that has been exposed to the activated synovial cells of patients with chronic polyarthritis shows complete degradation of collagen fibrilla. In the presence of prostane derivatives according to the invention, the degradation of collagen fibrilla is reduced.

The test system shows biochemically and electron-microscopically that the cartilage degradation induced by synovial cells of patients with chronic polyarthritis is reduced by the prostane derivatives of formula I or II according to the invention.

The prostane derivatives according to the invention exhibit the effect in the above-mentioned test at concentrations of 0.1 to 1000 ng/ml. The above-mentioned in vitro test system can be imparted to in vivo processes (cf.: J. J. STEINBERG et al. (1983) Biochem. Biophys. Acta 757: 47–58, further M. J. GROSSLEY and I. M. HUNNEYBALL daily dose of 0.1 to 200 mg of the prostane derivatives of general formula I or II according to the invention. Preferred are values of 0.3 to 60 mg per day, more preferred is 1 to 20 mg per day, and most preferred is 2 to 10 mg per day. The daily dose of prostane derivatives should be administered in 2 to 4 partial doses per day.

The prostane derivatives of general formula I or II can be administered by any usual method in the case of systemic treatment, especially enterally, preferably orally, and most preferably parenterally. Suppositories, tablets, capsules, drops, injection solutions, or suspensions are the appropriate forms for administration.

The prostane derivative iloprost is the especially preferred substance. It is administered, for example, in the case of large mammals, e.g., humans, in the above-represented type. In this cage, the doses are smaller by a factor of 2 than was previously indicated. The infusion solution as a continuous infusion in commonly used aqueous solvents, e.g., physiological common salt solution, is the form of administration preferred for systemic treatment. In this case, 0.01 ng/kg/min to 1.0 ng/kg/min is administered, preferably 0.03–0.3 ng/kg/min, and most preferably 0.1±0.05 ng/kg/min.

Since chronic polyarthritis also manifests itself in intermittent attacks, a prostane derivative is also to be administered during the symptom-free period. Thus, the prostane derivative according to the invention is used for prophylactic treatment. The dosages for prophylactic administration do not deviate significantly from those described above, but values that are lower by a factor of 2 to 4 than those that are used in the case of acute attacks are preferred.

This invention also relates to therapeutic compositions that contain a prostane derivative of general formula I or II together with at least one pharmaceutical vehicle, additive or diluent, which all are physiologically compatible. Such compositions can be produced in a way known in the art. Pharmacologically compatible and suitable adjuvants and vehicles are described, for example, in Remington's Pharmaceutical Science, 15th ed. Mack Publishing Company, Easton, Pa. (1980). Also, the use of cyclodextrin clathrates, which are listed in European Patent Specification EP 0 259 468, is possible.

By contrast with systemic treatment, topical application with a prostane derivative according to the invention, if appropriate with adjuvants and/or vehicles, is especially preferred.

The cardiovascular action is strongly felt at higher concentrations of prostane derivatives in the blood. Therefore, it is advantageous to apply the prostane derivatives according to the invention to the skin directly at the impaired joint. To this end, ointments, pastes, gels, or packs are suitable. This list is not exhaustive.

With topical application, the concentration of prostane derivatives in the joint in question is raised to a high value in a desired way, and simultaneously the concentration of prostane derivatives in the blood lies practically below the detection limit. The high bio-availability of the prostane derivatives results in quick penetration of the skin and the subjacent connective tissue, and the distribution of the prostane derivatives follows the law of diffusion. On the other hand, transport by convection current plays a completely insignificant role. The vessels that lie in or below the skin where the prostane derivatives are applied are either too small (venules, arterioles) or have too small an effective surface (veins, arteries) per skin part to cause a noticeable concentration of prostane derivatives in the blood.

EXAMPLE PART 1

Cell Cultures from Synovial Fluid

Cells from the synovial fluid of patients with chronic polyarthritis are co-cultivated in vitro with 4-day-old limb buds of mouse embryos (12 days old). After co-cultivation for about 7 days, degradation of the cartilage in the limb buds occurs, which can be reduced in the presence of the prostans derivatives according to the invention.

The substance iloprost is present in a final concentration of 100 ng/ml of culture medium in the cell cultures and is to be added to the cell cultures at the start.

Samples are taken on days 1 to 7. The culture conditions are described in detail in H. MOHAMED-ALI (1991) Z. Rheumatol. 50: 74–81; further in H. J. MERKER (1991) in Culture Techniques, D. NEUBERT and H. J. MERKER (eds.) Walter de Gruyter Verlag, Berlin—New York, pp. 119–133; further in H. B. FELL and R. W. JUBB (1977) Arthritis Rheuma 20: 1359–1371.

Instead of iloprost, the control batch contains only culture medium.

EXAMPLE PART 2

Measurement of Cartilage Degradation

Cartilage degradation is measured by the release of sulfated glycosaminoglycans, which are quantified as alcian blue glycosaminoglycan complex. The release of glycosaminoglycan is described in P. WHITEMAN (1973) Biochem J 131: 343–351. The samples taken on days 1 to 7 show the results listed in Table 2.

TABLE 2

| Day of Sampling: | 1 | 3 | 4 | 5 | 6 | 7 |
|---|---|---|---|---|---|---|
| Culture with iloprost[1] | 7 | 13 | 14 | 12 | 11 | 13 |
| Control[1] | 11 | 24 | 19 | 22 | 21 | 21 |

[1] = Value in µg of glucosaminoglucan per ml of medium

The prostane derivatives according to the invention reduce the release of glycosaminoglycans significantly.

EXAMPLE PART 3

Electron Microscope Evaluation

Electron microscope examination of cartilage that has been exposed to the activated synovial cells of patients with chronic polyarthritis shows complete degradation of collagen fibrilla. In the presence of prostane derivatives according to the invention, the degradation of collagen fibrilla is reduced.

The production of the electron microscope preparations and the histological evaluation are described in H. MOHAMED-ALI (1991) Z. Rheumatol. 50: 74–81; further in H. J. MERKER (1991) in Culture Techniques, D. NEUBERT and H. J. MERKER (eds.) Walter de Gruyter Verlag, Berlin—New York, pp. 119–133; further in H. B. FELL and R. W. JUBB (1977) Arthritis Rheuma 20: 1359–1371. In appearance the culture cells of patients with chronic polyarthritis treated with the prostane derivative according to the invention are approximately midway between cells from patients with chronic polyarthritis without prostane derivative treatment and cells from patients without chronic polyarthritis. The reduction of collagen degradation due to the preparations is estimated at 50%.

I claim:

1. A method for treating chronic polyarthritis which comprises administering to a subject in need thereof, a chronic polyarthritis treatment effective amount of a prostan compound of formula I or II

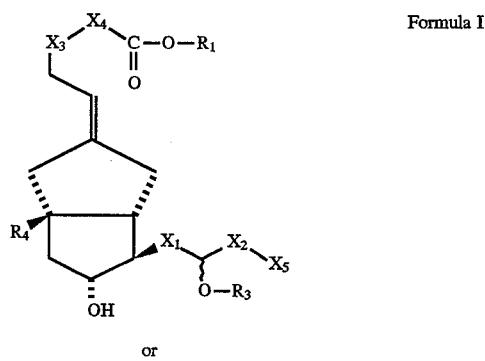

Formula I or

-continued

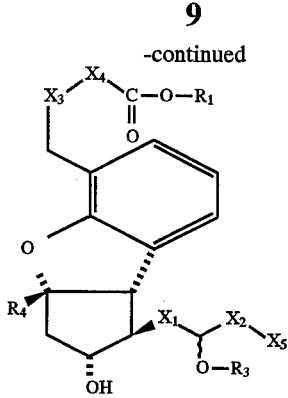

Formula II in which

X₁ is a —CH₂—CH₂—; trans —CH=CH— or a —C≡C— group,

X₂ is a straight-chain or branched, saturated alkylene group with 1 to 6 carbon atoms, X₃ is an —O— or —CH₂—, X₄ is —CH₂— or —[CH₂]₃—, X₅ —H or —C≡C—R₂;

R₁ is a hydrogen atom, an alkyl group with 1 to 6 carbon atoms, a cycloalkyl group with 5 or 6 carbon atoms, or a phenyl group, R₂ is a straight-chain or branched-chain, saturated or unsaturated alkyl group with 1 to 6 carbon atoms, R₃ is a hydrogen atom, an acyl radical with 1 to 4 carbon atoms, or a benzoyl radical, and R₄ is an —H or —CH₃;

in which the —O—R₃ group is in α- or β-position, or optionally a salt thereof with a physiologically compatible base, when R₁ is a hydrogen atom.

2. The method of claim 1, wherein the prostane compound is of the formula I in which X₁ is trans —CH=CH—, X₂ is a straight-chain or branched, saturated alkylene group with 2 to 4 carbon atoms, X₃ is —CH₂—, X₄ is —CH₂—, X₅ is —C≡C—R₂;

R₁ is a hydrogen atom, an alkyl group with 1 to 3 carbon atoms, or a phenyl group, R₂ is a straight-chain or branched-chain, saturated or unsaturated alkyl group with 1 to 3 carbon atoms, R₃ is a hydrogen atom or an acyl radical with 2 carbon atoms and R₄ is —H;

in which the —O—R₃ group is in α- or β-position, or optionally a salt thereof with a physiologically compatible base, when R₁ is a hydrogen atom.

3. The method of claim 2, wherein

X₁ is a trans —CH=CH— group,

X₂ is a methylethylene group in which the methyl group is connected to the first carbon atom of the ethylene group, X₃ is —CH₂—, X₄ is —CH₂—, X₅ is —C≡C—R₂;

R₁ is a hydrogen atom or a methyl group,

R₂ is a methyl or ethyl group,

R₃ is a hydrogen atom or a formyl group, and

R₄ is an —H;

in which the —O—R₃ group is in α- or β-position, or optionally a salt thereof with a physiologically compatible base, when Rx is a hydrogen atom.

4. The method of claim 3, wherein

X₁ is a trans —CH=CH— group,

X₂ is a methylethylene group, in which the methyl group is connected to the first carbon atom of the ethylene group, X₃ is —CH₂—, X₄ is —CH₂—, X₅ is —C≡C—R₂;

R₁ is a hydrogen atom,

R₂ is a methyl group,

R₃ is a hydrogen atom, and

R₄ is an —H;

in which the OH group is in α- or β-position, or optionally a salt thereof with a physiologically compatible base.

5. The method of claim 1, wherein the prostane compound is cicaprost or a salt thereof.

6. The method of claim 1, wherein the prostane compound is eptaloprost or a salt thereof.

7. The method of claim 1, wherein the prostane compound is ciprostene or a salt thereof.

8. The method of claim 1, wherein the prostane compound is beraprost or a salt thereof.

9. The method of claim 1, wherein the prostane compound is administered in a pharmaceutical composition further comprising pharmacological adjuvants or vehicles.

10. The method of claim 1, wherein the subject is a human or other mammal.

11. The method of claim 1, wherein the prostane compound is administered in a composition having a prostane compound concentration of 0.1 to 1000 ng/ml.

12. The method of claim 1, wherein the prostane compound is administered in a daily dose of 1 to 3000 µg/kg of the subject body weight.

13. The method of claim 1, wherein the subject is a human and the prostane compound is administered in a daily dose of 0.1 to 200 mg.

14. The method of claim 1, wherein the subject is a human and the prostane compound is administered in a daily dose of 0.3 to 60 mg.

15. The method of claim 13, wherein the daily dose is administered in 2 to 4 partial doses per day.

16. The method of claim 1, wherein the prostane compound is administered enterally or parenterally.

17. The method of claim 1, wherein the prostane compound is administered topically.

* * * * *